United States Patent
Querci et al.

(10) Patent No.: US 10,570,312 B2
(45) Date of Patent: Feb. 25, 2020

(54) METHOD FOR THE SEPARATION OF THE ISOPRENIC CONSTITUENTS OF GUAYULE

(71) Applicant: versalis S.p.A., San Donato Milanese (MI) (IT)

(72) Inventors: Cecilia Querci, Novara (IT); Danilo Del Prete, Oleggio (IT); Maria Caldararo, Trecate (IT); Gianni Girotti, San Giuliano Milanese (IT)

(73) Assignee: versalis S.p.A, San Donato Milanese (MI) (IT)

( * ) Notice: Subject to any disclaimer, the term of this patent is extended or adjusted under 35 U.S.C. 154(b) by 0 days.

(21) Appl. No.: 15/579,785

(22) PCT Filed: Jul. 29, 2016

(86) PCT No.: PCT/IB2016/054578
§ 371 (c)(1),
(2) Date: Dec. 5, 2017

(87) PCT Pub. No.: WO2017/021852
PCT Pub. Date: Feb. 9, 2017

(65) Prior Publication Data
US 2018/0171178 A1   Jun. 21, 2018

(30) Foreign Application Priority Data
Jul. 31, 2015   (IT) .................. 102015000040937

(51) Int. Cl.
*C09F 1/04*   (2006.01)
*C07C 67/56*   (2006.01)
(Continued)

(52) U.S. Cl.
CPC ............... *C09F 1/04* (2013.01); *B01D 9/005* (2013.01); *B01D 9/0018* (2013.01); *B01D 17/02* (2013.01);
(Continued)

(58) Field of Classification Search
CPC ......... C07C 69/92; C07C 67/14; C07C 67/52; C07C 67/56; C07C 67/58; C07C 69/618;
(Continued)

(56) References Cited

U.S. PATENT DOCUMENTS 4,739,038 A    4/1988 Schloman, Jr.
2009/0099309 A1   4/2009 Gumbs

FOREIGN PATENT DOCUMENTS

RU   2017 106 153 A   11/2018

OTHER PUBLICATIONS

Vivar et al , "Triterpenes in Parthenium Argentatum, structures of Argentatins C and D", Phytochemistry, 1990, vol. 29, No. 3, pp. 915-918.*

(Continued)

*Primary Examiner* — Frances Tischler
(74) *Attorney, Agent, or Firm* — Oblon, McClelland, Maier & Neustadt, L.L.P.

(57) ABSTRACT

Method for the separation of at least one isoprenic constituent from the resin of a plant of guayule and/or of the guayule type comprising the steps of: a) providing a defatted resin of guayule and/or of the guayule type; b) subjecting the defatted resin to partitioning of the liquid-liquid type with solvents that are immiscible in each other thus obtaining an apolar extract containing the isoprenic constituents guayulin A, guayulin B and argentatin B; and a polar extract containing the isoprene constituents argentatin A, argentatin C and argentatin D; and c) separating at least one isoprenic constituent from said polar extract and/or from the apolar extract thus obtained, wherein step c) comprises a step in which the polar extract is subjected to partitioning of the liquid-liquid type with solvents immiscible in each other and/or a step in which the apolar extract is subjected to partitioning of the solid-liquid type.

20 Claims, 4 Drawing Sheets

(51) Int. Cl.
  *C07C 67/58*  (2006.01)
  *C07J 53/00*  (2006.01)
  *C07J 71/00*  (2006.01)
  *C07C 67/52*  (2006.01)
  *C07C 29/09*  (2006.01)
  *B01D 9/00*  (2006.01)
  *B01D 17/02*  (2006.01)
  *C07C 67/03*  (2006.01)
  *C08C 1/04*  (2006.01)

(52) U.S. Cl.
  CPC ............ *C07C 29/095* (2013.01); *C07C 67/03* (2013.01); *C07C 67/52* (2013.01); *C07C 67/56* (2013.01); *C07C 67/58* (2013.01); *C07J 53/004* (2013.01); *C07J 71/0005* (2013.01); *C08C 1/04* (2013.01)

(58) Field of Classification Search
  CPC ... C07C 2602/32; C07C 29/095; C07C 67/03; B01D 17/02; B01D 9/0018; B01D 9/005; C07J 53/004; C07J 71/0005; C08C 1/04; C09F 1/04
  See application file for complete search history.

(56) References Cited

OTHER PUBLICATIONS

International Search Report and Written Opinion of the International Searching Authority dated Oct. 11, 2016 in PCT/IB2016/054578, citing documents AA, AB and AV—AX therein, 15 pages.
Carlos L. Céspedes, et al., "Insect Growth Regulatory Activity of Some Extracts and Compounds from Parthenium Argentatum on Fall Armyworm Spodoptera Frugiperda" A Journal of Biosciences, vol. 56, No. 1-2, Jan. 1, 2001, XP055253858, pp. 95-105.
Jerome H. Zoeller, Jr., et al., "Concise Multigram Purification of Guayulin A from Guayule", Journal of Agricultural and Food Chemistry, vol. 42, No. 8, XP055253749, Aug. 1, 1994, pp. 1647-1649.
William W. Schloman, Jr., et al., "Guayule Byproduct Evaluation: Extract Characterization" Journal of Agricultural and Food Chemistry, vol. 31, No. 4, XP055253748, Jul. 1, 1983, pp. 873-876.
Combined Office Action and Search Report dated Aug. 5, 2019 in Chinese Patent Application No. 201680036396.2 (with English translation).
Office Action dated Sep. 20, 2019 in Russian Patent Application No. 2018105348, citing documents AO therein, 16 pages (with English translation).

\* cited by examiner

METHOD FOR THE SEPARATION OF THE ISOPRENIC CONSTITUENTS OF GUAYULE

FIELD OF APPLICATION

The present invention generally relates to the industry sector of the extraction and the processing of rubber, in particular of the rubber of guayule and/or of the guayule-type plants, more particularly in the field of recovery of its waste products.

In particular, the invention refers to a method for the separation of the isoprenic constituents from the guayule resin or from the guayule type resin, among which guayulin A and B, and argentatin A, B, C and D.

Prior Art

The guayule (*Partenium argentatum*) is a perennial shrub native of the semi-arid regions of northern Mexico and Texas.

It has a variable content of cis-1,4-polyisoprene rubber depending on several factors and between about 5 and 20% on the dry plant. Because of the high importation costs of the rubber extracted from other natural sources such as *Hevea brasilensis*, guayule was taken into account already before the second World War, both in the United States and in Italy, as an alternative source of natural rubber.

Guayule rubber differs from that of *Hevea brasiliensis* for some essential aspects, the most relevant is referred to a significantly lower protein content that gives hypoallergenic features to the natural rubber. In fact, *Hevea* latex allergy is caused by a protein called pro-hevein, which has a role for the latex coagulation in the plant; it binds the IgEs hevein epitope triggering the immune response, which determines a series of skin and respiratory allergic reactions.

Other suitable plants for the extraction of rubber similar to that one extracted from guayule comprise, for example, *Euphorbia lathyris, Parthenium incanum, Chrysothamnus nauseosus, Pedilanthus macrocarpus, Cryptostegia grandiflora, Asclepias syriaca, Asclepias speciosa, Asclepias subulata, Solidago altissima, Solidago gramnifolia, Solidago rigida, Cacalia atriplicifolia, Taraxacum koksaghyz, Pycnanthemum incanum, Teucreum canadense, Campanula americana.* Furthermore, other plants belong to the Asteraceae (Compositae), Euphorbiaceae, Campanulaceae, Labiatae and Moraceae genera.

Currently, guayule is considered not only as a possible source of hypoallergenic natural rubber and particularly in the last years several studies aimed to develop methods and technologies such that to allow a complete exploitation of all plant components, among which resin, were carried out.

In fact guayule resin, produced in a comparable or higher amount than that of rubber, can be used for several applications among which, for example, the adhesives manufacture and the production of wooden panels resistant to parasite damage, while, after the extraction of the natural rubber and/or resin, the residual guayule biomass can be used in the manufacture of combustible pellets and briquettes and as source of so-called "second generation sugars" (from cellulose and hemicellulose fractions of said residual biomass) then fermentable to bio-ethanol and/or bio-fuels.

Resin produced by the guayule plant, as well as from other plants from which a gum and a resin similar to that one of guayule are obtained, among which those listed above, is rich of secondary metabolites among which the isoprenic constituents belonging to the terpene family (see table 1). Guayulins are sesquiterpene compounds of potential interest for the fragrance industry and for the production of insect pheromones s, whereas argentatins are triterpene compounds with a potential antioxidant and antitumor activity. The guayule processing techniques developed so far are mainly focused on the extraction processes of the cis-1,4-polyisoprene natural rubber and of the crude resin, on their treatment and on the processes of biomass conservation.

TABLE 1

| Isoprenic constituents of interest | | |
|---|---|---|
| Constituent | Classification | Molecular structure |
| Guayulin A | Sesquiterpene | <br>Guayulina A |
| Guayulin B | Sesquiterpene | <br>Guavulin B |

TABLE 1-continued

Isoprenic constituents of interest

| Constituent | Classification | Molecular structure |
| --- | --- | --- |
| Argentatin A | Triterpene | <br>Argentatina A |
| Argentatin B | Triterpene | <br>Argentatina B |
| Argentatin C | Triterpene | <br>Argentatina C |
| Argentatin D | Triterpene | <br>Argentatina D |

On the specific issue of the guayule resin (or the like) and even more in particular of its constituents, no detailed studies have been carried out so far, both due to the nature of the biomass, considered waste of natural rubber processing, but above all to the difficulty to have access to its constituents in pure form and with simple and cheap systems.

In fact, the methods known in the art provide for the use of chromatographic (column) purification processes which are expensive, as well as difficult to scale-up in view of the subsequent industrial application. The difficulty in separation and purification lies in the fact that the resin is constituted by a complex mixture of compounds of different nature which includes, in addition to metabolites such as fats, waxes and low molecular weight rubbers, also a number of secondary isoprenic metabolites.

Schloman et al. (1983) have described the quantification of guayulins and argentatins starting from the resin of the guayule plant (*Parthenium argentatum*). The guayulins were recovered by saponification with "short path" distillation followed by crystallization. The quantification was performed by means of chromatography methods (HPLC) (Schloman, W. W., Jr.; Hively, R. A.; Krishen, A.; Andrews, A. M. Guayule by product evaluation: extract characterization *J. Agric. Food Chem.* 1983, 31, 873-876).

A method of production of guayulin A and B has been described by Zoeller (1994) and makes use of chromatographic techniques (Zoeller, Jr. J. H., Wagner, J. P., Sulikowski, G. A. Concise multigram purification of guayulin A from guayule. *J. Agric. Food Chem.* 1994, 42, 1647-1649). This method consists of several steps: extraction of the guayule resin by means of two extraction processes in a suitable reactor with acetone under reflux for one hour; concentration of the crude extract by the complete evaporation of the solvent; separation of the low molecular weight rubbers, wherein the crude extract is dissolved in ethyl acetate and subjected to a liquid/liquid partitioning with brine, followed by anhydrification of the organic phase and removal of the solvent by evaporation under vacuum to obtain an oily green compound; chromatographic fractionation of the resin by gravimetric chromatography on silica gel; chromatographic purification of the guayulin A with a further process of gravimetric chromatography on silica gel. After concentration of the collected fractions, a precipitate of guayulin A as a pure white solid with a yield of 1% on the crude extract and a mixture of A and B guayulins are obtained. The separation or the isolation of argentatins is not provided by this method.

The above said method described by Zoeller et al., 1994, has some drawbacks, among which low yields of pure guayulin obtained. In fact, pure guayulin A is obtained with a yield of 1% on the crude extract, whereas guayulin B is obtained in mixture with guayulin A and its purification is difficult.

Another drawback of the method is constituted by the purification of only one of its components, namely guayulin A.

Conversely, guayulin B was obtained in a pure form by Firestone Tire and Rubber Co., but with a yield of only 0.4% from the resin, by means of chromatographic techniques (Singh, M. Bagwa Guayule resin separation and purification M. S. Thesis, Texas A&M University, Department of Nuclear Engineering, December 1992).

Therefore, the technical problem dealt with by the present invention is to provide for a method which is practical, inexpensive, versatile, scalable and with high yield for the separation of isoprenic components from the resin of guayule plant, in particular guayulin A, guayulin B, argentatin A, argentatin B, argentatin C and/or argentatin D.

SUMMARY OF THE INVENTION

Said problem has been solved according to the invention by a method for the separation of at least one isoprenic constituent from the resin of a guayule and/or of the guayule type plant comprising the steps of:
a) providing a defatted resin of guayule and/or of the guayule type;
b) subjecting the defatted resin to partitioning of the liquid-liquid type with solvents that are immiscible in each other thus obtaining an apolar extract containing the isoprenic constituents guayulin A, guayulin B and argentatin B; and a polar extract containing the isoprenic constituents argentatin A, argentatin C and argentatin D; and
c) separating at least one isoprenic constituent from said polar extract and/or from said apolar extract thus obtained, wherein the step c) comprises a step in which the polar extract is subjected to partitioning of the liquid-liquid type with solvents immiscible in each other and/or a step in which said apolar extract is subjected to partitioning of the solid-liquid type.

Herein, the term "defatted resin" means a resinous extract of guayule plant substantially free of waxes, fats and low molecular weight rubbers.

Herein, the terms "partitioning of the liquid-liquid type" and "liquid-liquid partitioning" mean a process of separation of one or more compounds present in a complex mixture that takes advantage of the different solubility of the compounds to be separated in two solvents immiscible in each other.

Herein, the terms "partitioning of the liquid-solid type" and "liquid-solid partitioning" means the operation of extraction based on the affinity of a solid phase for one or more constituents present in a complex mixture.

In fact, in the partitioning (or extraction) of the liquid-solid type (commonly indicated with the SPE acronym, from the English denomination solid-phase extraction), the distribution of the constituents, between a liquid phase and a solid phase insoluble in the solution with which it is placed into contact, is used. After the contact for a suitable period of time, the liquid phase is removed and the compounds absorbed on the solid phase, can be recovered by using an extracting solution.

Preferably, said at least one isoprenic constituent (also indicated as non-polymeric isoprenoid) is selected from the group that comprises guayulin A, guayulin B, argentatin A, argentatin B, argentatin C, argentatin D, and mixtures thereof.

Preferably, in step a) the defatted resin is obtained from the plant of guayule or of the guayule type, more preferably from one or more plants chosen in the group comprising *Parthenium argentatum, Euphorbia lathyris, Parthenium incanum, Chrysothamnus nauseosus, Pedilanthus macrocarpus, Cryptostegia grandiflora, Asclepias syriaca, Asclepias speciosa, Asclepias subulata, Solidago altissima, Solidago gramnifolia, Solidago rigida, Cacalia atriplicifolia, Taraxacum koksaghyz, Pycnanthemum incanum, Teucreum canadense* and *Campanula americana*, preferably *Parthenium argentatum*.

The defatted resin of step a) can be obtained starting from a fresh or dried plant, natural or cultivated in vitro.

According to an embodiment, the defatted resin of step a) is obtained starting from a crude extract of the whole plant.

According to an alternative embodiment, the defatted resin of step a) is obtained starting from a crude extract of one or more among branches, stem, and leaves of the plant.

According to a further alternative embodiment, the defatted resin of step a) is obtained starting from a crude extract of the bagasse.

Herein, the term "crude extract" refers to the fraction of the plant of guayule or of the guayule type containing the resin that is obtained after the treatment of the plant, usually with solvents, in order to separate from the lignocellulosic components the desired fraction of the plant containing the resin.

The term "bagasse" refers to the residual biomass derived from the processes of extraction of the guayule natural rubber.

Preferably, the defatted resin of step a) is obtained by a defatting step, more preferably a fractionated crystallization step (also called "winterization") of a crude extract of a plant of guayule or of the guayule type.

Advantageously, after the defatting step, the yield of defatted resin, expressed as percentage of the resin dry weight of the resin with respect to the dry weight of the crude extract, is between 50 and 70%, more preferably about 60%. Preferably, the fractioned crystallization step (or "winterization") comprises a treatment at a temperature between 30 and 50° C., more preferably 40° C., of the crude extract with a solvent, preferably under stirring up to the substantially complete dissolution of the crude extract; and subsequent cooling, preferably at a temperature of about 0° C., thus obtaining the separation of an apolar component, comprising waxes, fats and low molecular weight rubbers, from a polar component (also called "mother liquors") comprising the defatted resin.

Preferably, in the fractionated crystallization step, the solvent is selected from methanol, water, ethanol, methanol, acetone and combinations thereof, preferably methanol.

Preferably, in the fractionated crystallization step, the crude extract is suspended in the solvent in a ratio, expressed as dry weight (g) of the crude extract with respect to the volume (l) of the solvent, between 50 and 150 g/l, more preferably of 100 g/l.

Preferably the step b) is preceded by a step of concentration of the defatted resin to a volume, expressed as volume/volume percentage of the resin before the concentration, between 5 and 20% (v/v), more preferably between 5 and 10% (v/v).

Preferably, in said step b), the partitioning of the liquid-liquid type is carried out at a temperature between 15° C. and 26° C., more preferably at 20° C.

Preferably, in said step b), the solvents immiscible in each other comprise a polar solvent and an apolar solvent.

Preferably, in step b) the polar solvent is selected from the group comprising water, methanol, ethanol, isopropanol, tert-butanol, ethyl acetate, and combinations thereof, more preferably a solution of methanol and water; more preferably in a volume ratio between methanol and water between 2:1 and 6:1, more preferably between 3:1 and 5:1, even more preferably about 4:1; and the apolar solvent is chosen between petroleum ether, n-hexane and combinations thereof, more preferably petroleum ether.

Preferably, the polar solvent is in a volume ratio with respect to the apolar solvent between 2:1 and 8:1, more preferably between 4:1 and 5:1.

Preferably, the step b) of subjecting the defatted resin to partitioning is repeated one or more times.

Preferably, the step b) comprises a drying step of the thus obtained apolar extract, more preferably at a pressure between 1.5 mbar and 2.0 mbar and at a temperature between 25° C. and 35° C.

Preferably, the yield of the total of the guayulin A, guayulin B and argentatin B in the apolar extract obtained in step b), expressed as dry weight percentage with respect to the dry weight of the defatted resin of step a) is at least 10.0%, more preferably at least 12.0%.

Preferably, the yield of the total of argentatin A, argentatin C and argentatin D in the polar extract obtained in step b), expressed as dry weight percentage with respect to the dry weight of the defatted resin of step a) is at least 6.0%, more preferably at least 11.0%.

Preferably, in the step c), the at least one isoprenic constituent is selected from guayulin A, guayulin B, argentatin B or mixtures thereof and step c) comprises a step of subjecting the apolar extract obtained in the step b) to partitioning of the solid-liquid type.

Preferably, in the step c), the partitioning of the solid-liquid type comprises the steps of subjecting the apolar extract obtained in step b), dissolved in a combination of two solvents miscible in each other, to adsorption on a solid matrix, more preferably by selective trapping; and of treatment, more preferably rinsing, of the solid matrix thus obtained with a combination of two solvents miscible in each other, thus obtaining a solution containing a mixture of guayulin A and guayulin B, and a solid matrix containing argentatin B.

Preferably, the treatment of the solid matrix thus obtained is carried out with a combination of solvents that is the same of the combination of solvents of adsorption step on solid matrix.

Preferably, the adsorption step on the solid matrix is followed by the evaporation of the combination of solvents.

Preferably, the adsorption on the solid matrix is carried out into a reaction flask or on a filtering support, more preferably in a reaction flask.

Preferably, the adsorption on the solid matrix is carried out at a pressure between 1.0 mbar and 2.5 mbar, more preferably between 1.5 mbar and 2.0 mbar and at temperature between 25° C. and 35° C., more preferably between 28° C. and 32° C.

Preferably, the solid matrix is selected from the group comprising: basic silica gels, silica gels bonded to hydrocarbons having $C_8$-$C_{18}$ alkyl groups (i.e. reversed phase), silica gels bonded to cyanide groups or equivalent, silica gels bonded to phenyl alkyl groups or equivalent, and combinations thereof, more preferably basic silica gel.

Preferably, in the partitioning of the solid-liquid type of step c), the combination of solvents is a combination of a polar solvent and an apolar solvent, more preferably in a volume ratio with respect to the apolar solvent and the polar solvent between 4:1 and 49:1, more preferably between 5.5:1 and 19:1, even more preferably of about 9:1.

Preferably, the solid matrix has a mesh size between 70 and 230.

Preferably, the ratio, expressed as volume/volume percentage, between the combination of solvents and the solid matrix is between 1:5 and 1:2, more preferably between 1:4 and 1:3.

Preferably, in the partitioning of the solid-liquid type of step c), in the combination of solvents, the solvents are mixed with the apolar extract obtained in step b) in a ratio, expressed as combination volume of solvents with respect to the dry weight of the apolar extract, between 5 and 9 ml/g, more preferably 7 ml/g.

Preferably, in the partitioning of the solid-liquid type of step c), the polar solvent is selected from the group comprising: ethanol, methanol, acetone, acetic acid, ethyl acetate, acetonitrile, dichloromethane, and combinations thereof; and the apolar solvent is selected from the group comprising: petroleum ether and n-hexane and combination thereof.

Preferably, the yield of the mixture of guayulin A and guayulin B in the solution containing the mixture of guayulin A and guayulin B obtained in step c), expressed as dry weight percentage with respect to the dry weight of the defatted resin of step a) is at least 5.0%, more preferably at least 8.0%.

Preferably, the yield of argentatin B in the solid matrix obtained in step c), expressed as dry weight percentage with respect to the dry weight of the defatted resin of step a) is at least 2.0%, more preferably at least 3.2%.

Preferably, the solid matrix containing argentatin B is subjected to a further treatment, preferably rinsing with a polar solvent, thus obtaining a solution of argentatin B.

Preferably, in the further treatment of the solid matrix, the polar solvent is selected from the group comprising ethanol, methanol, acetone, acetic acid, ethyl acetate, acetonitrile, dichloromethane, and combinations thereof, preferably ethyl acetate.

Preferably, the further treatment of the solid matrix is carried out at a temperature between 15° C. and 30° C., more preferably between 20° C. and 25° C.

Preferably, the further treatment of the solid matrix is followed by a step of filtration and drying of the solution of argentatin B thus separated.

Preferably, in step c), the at least one isoprenic constituent is chosen from argentatin A, argentatin C, argentatin D or mixtures thereof and the step c) comprises a step of subjecting the polar extract obtained in step b) to partitioning of the liquid-liquid type.

Preferably, in step c), the partitioning of the liquid-liquid type comprises the step of subjecting the polar extract obtained in step b) to separation in a combination of a polar solvent and an apolar solvent thus obtaining an organic phase containing argentatin A and an aqueous phase containing a mixture of argentatin C and argentatin D.

Preferably, in the partitioning of the liquid-liquid type of step c), the apolar solvent and the polar solvent are in a volume ratio of the apolar solvent with respect to the polar solvent comprised between 1:2 and 1:8, more preferably between 1:5 and 1:7, even more preferably of about 1:6.

Preferably, in step c), the partitioning step of the liquid-liquid type is repeated one or more times.

Preferably, in the partitioning step of the liquid-liquid type of step c), the apolar solvent is selected from the group comprising cyclohexane, n-hexane, petroleum ether and combinations thereof, more preferably cyclohexane.

Preferably, in the partitioning step of the liquid-liquid type of step c), the polar solvent is selected from the group comprising water, methanol, ethanol, isopropanol, tert-butanol, and combinations thereof, preferably methanol and water.

Preferably, in the partitioning of the liquid-liquid type of step c), the polar solvent comprises the suspension solvent of the polar extract obtained in step b).

Preferably, in the step of partitioning of the liquid-liquid type of step c), the partitioning of the liquid-liquid type is preceded by a step of concentration of the polar extract obtained in step b).

Preferably, the organic phase containing the argentatin A so obtained is dried.

Preferably, the aqueous phase containing a mixture of argentatin C and argentatin D is further treated with a polar solvent and more preferably it is dried.

Preferably, the yield of argentatin A in the organic phase obtained in step c), expressed as dry weight percentage with respect to the dry weight of the defatted resin of step a) is at least 3.0%, more preferably at least 8.0%.

Preferably, the yield of the mixture of argentatin C and argentatin D in the aqueous phase obtained in step c), expressed as a dry weight percentage with respect to the dry weight of the defatted resin of step a) is at least 0.5%, more preferably at least 3.0%.

Preferably, step c) is followed by at least a step d) of purification of at least one said isoprenic constituent.

Preferably, the purification step d) comprises a crystallization step of at least one isoprenic constituent, thus obtaining at least one isoprenic constituent of the resin in a substantially pure crystalline form.

Preferably, in step d), the crystallization step is a direct crystallization with apolar solvents, more preferably petroleum ether and/or n-hexane, at low temperatures, more preferably at a temperature equal to or lower than 0° C.

Preferably, in the crystallization step of the guayulin A, argentatin A, C and D, the temperature of crystallization is about −23° C.

Preferably, the step d) comprises a step d1) wherein the mixture of guayulin A and guayulin B obtained in step c) is subjected to precipitation of guayulin A by treatment with an apolar solvent, preferably selected from the group that comprises petroleum ether, n-hexane and combinations thereof, even more preferably n-hexane, with cooling, more preferably at a temperature between 0 and −23° C., even more preferably −23° C., thus obtaining a precipitate of purified guayulin A and a supernatant containing a mixture of guayulin A and guayulin B.

Preferably, the precipitate of purified guayulin A is subjected to crystallization, more preferably by direct crystallization with n-hexane, thus obtaining crystals of pure guayulin A.

Preferably, the yield of pure guayulin A, expressed as dry weight percentage with respect to the dry weight of the defatted resin of step a), is at least 2.0%, more preferably at least 5.0%.

Preferably, the yield of the mixture of guayulin A and guayulin B obtained in step d1), expressed as dry weight percentage with respect to the dry weight of the defatted resin of step a), is at least 0.5%, more preferably at least 2.8%.

Preferably, the step d) comprises a step d2) wherein the argentatin B obtained in step c) is subjected to precipitation with an apolar solvent, preferably selected from the group that comprises petroleum ether, n-hexane and combinations thereof, even more preferably petroleum ether, with cooling, more preferably at a temperature between 0 and −23° C., even more preferably 0° C., thus obtaining a precipitate of purified argentatin B.

Preferably, the precipitate of purified argentatin B is subjected to crystallization, more preferably by direct crystallization with petroleum ether, thus obtaining crystals of pure argentatin B.

Preferably, the yield of the pure argentatin B, expressed as a dry weight percentage with respect to the dry weight of the defatted resin of step a), is at least 1.5%, more preferably at least 3.4%.

Preferably, the step d) comprises a step d3) wherein the argentatin A obtained in step c) is subjected to precipitation with an apolar solvent, preferably selected from the group that comprises cyclohexane, n-hexane, ethyl ether, petroleum ether, and combinations thereof, even more preferably ethyl ether and n-hexane, with cooling, more preferably at a temperature between 0 and −23° C., even more preferably −23° C., thus obtaining a precipitate of purified argentatin A.

Preferably, the precipitate of purified argentatin A is subjected to crystallization, more preferably by direct crystallization with n-hexane and ethyl ether, thus obtaining crystals of pure argentatin A.

Preferably, the crystallization of the precipitate of purified argentatin A is carried out at a temperature between 0 and −78° C.

Preferably, the step d) comprises a step d4) wherein the mixture of argentatin C and argentatin D obtained in step c) is subjected to precipitation of argentatin D with an apolar solvent, preferably selected from the group that comprises petroleum ether, n-hexane and combinations thereof, even more preferably petroleum ether, with cooling, more preferably at a temperature between 0 and −23° C., even more preferably −23° C., thus obtaining a precipitate of purified argentatin D and a supernatant containing argentatin C.

Preferably, the precipitate of purified argentatin D is subjected to crystallization, more preferably by direct crystallization with petroleum ether, thus obtaining crystals of pure argentatin D.

Preferably, the yield of the pure argentatin D, expressed as dry weight percentage with respect to the dry weight of the defatted resin of step a), is at least 0.3%, more preferably at least 0.8%.

Preferably, step d4) is followed by a step d5) wherein the supernatant containing argentatin C is subjected to evaporation of the solvent and the residue is dissolved in an apolar solvent, preferably selected from the group that comprises cyclohexane, petroleum ether, ethyl ether, n-hexane and combinations thereof, even more preferably ethyl ether, with cooling, more preferably at a temperature between 0 and −23° C., more preferably −23° C., thus obtaining a precipitate of purified argentatin C.

Preferably, the precipitate of purified argentatin C is subjected to crystallization, more preferably by direct crystallization with n-hexane, thus obtaining crystals of pure argentatin C.

Preferably, the yield of the pure argentatin C, expressed as dry weight percentage with respect to the dry weight of the defatted resin of step a), is at least 0.1%, more preferably at least 0.3%.

Preferably, the step d4) is preceded by a step of concentration of the aqueous phase obtained in step c).

Preferably, the step c) is followed by a step e1) comprising a basic hydrolysis reaction of the guayulin A obtained in step d1) and/or of the mixture of guayulin A and guayulin B obtained in step c) thus obtaining a solution containing partheniol.

Preferably, the basic hydrolysis reaction is carried out in a reaction mixture comprising the guayulin A and/or the mixture of guayulin A and guayulin B and a basic solution; wherein the basic solution is more preferably selected from the group comprising potassium hydroxide, sodium hydroxide and combinations thereof, more preferably potassium hydroxide, wherein the guayulin A and/or the mixture of guayulin A and guayulin B and the basic solution are in a weight (g) on volume (ml) ratio of the guayulin A and/or the mixture of guayulin A and guayulin B with respect to the basic solution between 1:2 and 1:10, more preferably between 1:1.5 and 1:10, even more preferably of about 1:5, more preferably under stirring, thus obtaining an organic phase containing partheniol.

Preferably, the reaction mixture further comprises methanol and water, wherein the ratio volume/volume between water and methanol is between 1:20 and 1:100 and more preferably between 1:50.

Preferably, the solution containing partheniol is subjected to crystallization, more preferably by direct crystallization with petroleum ether, with cooling, more preferably at 0° C., thus obtaining pure partheniol.

Preferably, the yield of the pure partheniol obtained by hydrolysis of the mixture of guayulin A and guayulin B of step d1), expressed as dry weight percentage with respect to the dry weight of the defatted resin of step a), is at least 0.5%, more preferably 1.5%.

Preferably, the step e1) is followed by a step e2) of esterification of the thus obtained partheniol, thus obtaining a solution containing guayulin B.

Preferably, the esterification of the partheniol is carried out with anisic acid or anisoyl chloride.

Preferably, in the esterification step of the parteniol, the anisic acid or the anisoyl chloride are used in an amount of 1 equivalent respect to the partheniol.

Preferably, the solution containing guayulin B thus obtained in step e2) is subjected to evaporation and the residue is dissolved in an apolar solvent, preferably selected from the group that comprises cyclohexane, n-hexane, ethyl ether, petroleum ether and combinations thereof, even more preferably petroleum ether, thus obtaining a precipitate of purified guayulin B.

Preferably, the precipitate of purified guayulin B is subjected to crystallization, with cooling, more preferably at a temperature between 0 and −23° C., more preferably 0° C., thus obtaining crystals of pure guayulin B.

Preferably, the yield of the pure guayulin B, expressed as dry weight percentage with respect to the dry weight of the defatted resin of step a), is at least 0.55% (reaction yield 38% molar of the reaction).

Preferably, the step c) is followed by a step e3) that comprises a reduction reaction of the argentatin B obtained in step c) and/or in step d2), thus obtaining a solution containing argentatin D.

Preferably, the reduction reaction is carried out in a reaction mixture comprising the argentatin B and lithium aluminum hydride $LiAlH_4$ or sodium borohydride, more preferably sodium borohydride $NaBH_4$, wherein preferably the reaction mixture has a concentration, expressed as dry weight of argentatin B with respect to the volume of the mixture, comprised between 2.5 and 1.5 g/100 ml, more preferably 2.0 g/100 ml, more preferably under stirring, thus obtaining a solution containing argentatin D.

Preferably, in the reduction reaction, the lithium aluminum hydride $LiAlH_4$ or sodium borohydride are in an amount equal to 3 equivalents with respect to the argentatin B.

Preferably, the reaction mixture further comprises methanol, wherein the methanol is in a concentration expressed as weight (g) percentage on volume (ml) comprised between 70 and 90%, more preferably 80%.

Preferably, following the reduction reaction, the solution containing argentatin D thus obtained is subjected to evaporation and the residue is dissolved in an apolar solvent, preferably selected from the group that comprises cyclohexane, ethyl ether, n-hexane, petroleum ether and combinations thereof, even more preferably petroleum ether, thus obtaining a precipitate of purified argentatin D.

Preferably, the precipitate of purified argentatin D is subjected to crystallization, with cooling, more preferably at a temperature comprised between 0 and −23° C., more preferably 0° C., thus obtaining crystals of pure argentatin D.

Preferably, the yield of the pure argentatin D, expressed as dry weight percentage with respect to the dry weight of the defatted resin of step a), is at least 0.50%, more preferably at least 0.8%.

The structures of the purified compounds obtained according to the present invention are determined by analysis and spectroscopic characterization according to the methods known in the art.

In fact, it has been found that, by subjecting the guayule (or of the guayule type) resin and resin extraction products to appropriate separations with solvents, in particular partitionings of the liquid-liquid and/or liquid-solid type, it is possible to separate and purify all the isoprenic constituents of interest, guayulin A, guayulin B, argentatin A, argentatin B, argentatin C and argentatin D, with higher yield with respect to the known techniques.

The known techniques, in fact, are based on column chromatographic methods, which are expensive and which cannot be scaled-up to an industrial scale.

Furthermore, the prior art does not describe the separation or the isolation of argentatins, of considerable interest too, for the applications in the pharmaceutical field.

Conversely, the Applicant was able to identify a method that, using the characteristics of polarity of the molecules of interest, and based on a precise sequence of steps and selection of solvents to each step, allows to separate and purify in a rapid, simple, versatile and inexpensive manner all the molecules of interest.

For example, the method of the present invention allows processing 1 Kg of crude resin in two days, thus obtaining about 30 g of guayulin A, 20 g of argentatin B and 3 g di argentatin A in a pure form.

Furthermore, the method of the present invention has no volume limits, thus being able to be applied also to industrial scale volumes.

Therefore, for the first time, it was possible to provide the constituents guayulin A, guayulin B, argentatin A, argentatin B, argentatin C, and argentatin D, to a purity degree and volumes so that to allow to study their characteristics and their industrial applications on a large scale.

The above-mentioned molecules can have interesting applications in various fields among which the essence-field, agricultural-field, cosmetic field and pharmaceutical field.

Furthermore, the method of the present invention, through semi-synthesis reactions, allows to obtain minor isoprenoids which are difficult to be obtained from the resin, such as guayulin B and argentatin D, which otherwise would not be separable in satisfactory amounts.

These semi-synthetic products represent a rational way in order to obtain natural and synthetic products having a high potential as for the industrial applicability, starting from products separated and purified thanks to the method of the present invention, which is more versatile and eco-sustainable with respect to the laborious and expensive methods already described in the prior art.

A peculiar feature of the whole method of the present invention is represented by the absence of column chromatographic techniques, yet allowing at the same time, according to preferred embodiments, to obtain crystalline products further purified by direct crystallization with apolar solvents at low temperature. The versatile and efficient separation obtained through the present invention is unexpected as apparently in contrast to the theories commonly accepted and described in the prior art, according to which instead, expensive steps of column chromatographic purification, in order to obtain results comparable to those ones obtained according to the method of the present invention, would be necessary.

However, if desired, the steps of purification of the present invention are suitable to be applied also to products not completely separated or purified, previously subjected to chromatography.

The method of the present invention allows reducing the number of the steps for the separation and purification of the constituents with respect to the methods known in the art, thus making the method simpler and versatile and at the same time optimizing the yields of obtaining pure products, as well as costs and times spent. Furthermore, the method of the present invention does not require the use of dangerous solvents.

The method of the present invention is applicable to resin obtained starting from all the parts of the plant without any specific precaution. In fact, the method can be applied not only on the resin obtained starting from the whole plant, but also starting from leaves, branches or stems (considered together or alone), as well as even from cell cultures thereof.

Thanks to the method of the present invention, a significant increase in terms of yield is obtained (5% of pure guayulin A according to the method of the present invention with respect to 1% of the method of Zoeller et al. 1994).

Through the method of the present invention it is possible to use and take advantage of the potentiality of the products obtained, thus recovering a material traditionally considered a waste material of the guayule plant processing in order to obtain the natural rubber.

The method of the present invention further provides an interesting solution to the problems of obtaining and accessibility of the non-polymeric isoprenoid compounds of guayule making available pure products which can be chemically modified in order to provide structural analogue of potential interest in various fields of application.

DETAILED DESCRIPTION OF THE INVENTION

The invention will be now further described with reference to some embodiments by way of example only, and are not limitative of the present invention.

All the indicated percentages are expressed as weight percentages and all the proportions of the mixtures of solvents are expressed as proportions by volume, unless otherwise indicated.

EXAMPLE 1

Figure 1:
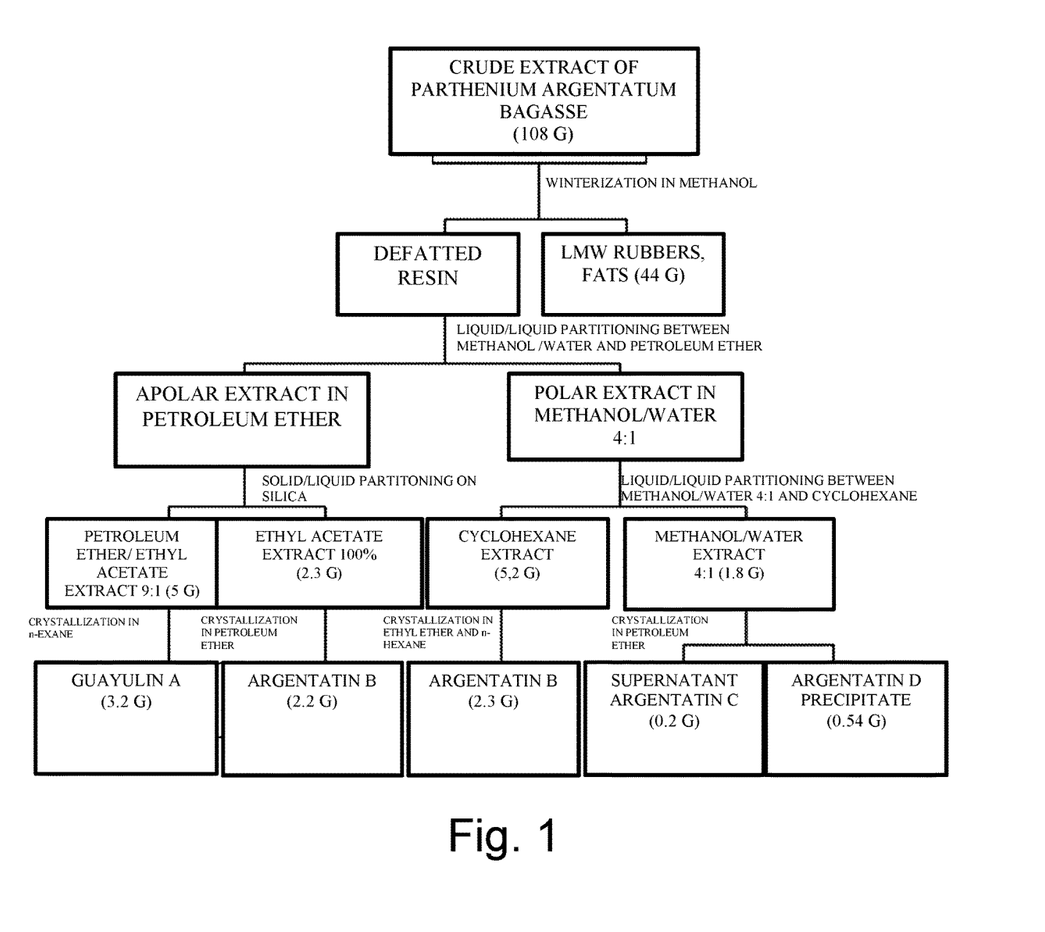
FIG. 1 represents a complete block-diagram of an embodiment of the method of the present invention, starting from a crude extract obtained from the bagasse of *Parthenium argentatum*. The numbers in brackets represent the amount of product expressed in grams.

Winterization of the crude extract of *Parthenium argentatum* (FIG. 1)

108 g of crude extract obtained from the bagasse of *Parthenium argentatum* were slowly dissolved under continuous stirring at 40° C. in methanol (800 mL) by using a volume of solvent of 1.0 L/100 g of crude extract.

After the complete dissolution the mixture was cooled at room temperature for 1 hour and then at 0° C. for 24 hours. A compact precipitate was formed and then recovered by filtration under 1.5 mbar.

The residue having a gummy consistency was then washed with methanol, cooled to 0° C. and air-dried at room temperature obtaining 44 g of fats and rubbers with a low molecular weight.

The polar liquid fraction (mother liquors) containing the defatted resin was recovered for the subsequent steps.

EXAMPLE 2

Partitioning of the liquid-liquid type of the resin (FIG. 1)

800 mL of methanol solution obtained from the process of winterization, for separating the lipophilic component of the crude resin, were diluted to a final volume of 1 L with 200 mL of water obtaining a mixture of methanol/water 4:1.

The obtained mixture was subjected to a partitioning process with petroleum ether (200 mL). After having reached the equilibrium between the phases, the organic phase was separated from the aqueous phase.

The latter was extracted again with 200 mL of petroleum ether for 3 times. The resultant organic phase was then washed with 200 mL of a mixture of methanol/water (4:1), recovered, anhydrified and concentrated under low pressures up to the complete drying thus obtaining 7.7 g of product.

The partitioning process was monitored by TLC (Thin layer chromatography).

EXAMPLE 3

Solid-liquid partitioning of the apolar extract (FIG. 1)

7.7 g of apolar extract obtained by the liquid-liquid partitioning process of 108 g of crude resin were dissolved in 60 mL (~7 mL/g) of a mixture of petroleum ether and ethyl acetate 9:1 and adsorbed on a bed of 200 mL of silica gel (70-230 mesh, 25 mL/g).

The solvent was removed from the suspension by evaporation under reduced pressure or vacuum filtration, and the resultant solid matrix was washed three times with 100 mL of the solvent mixture used for the absorption.

This operation was carried out into a reaction flask according to a method known to the person skilled in the art. The de-absorption solution was evaporated, thus obtaining a mixture of guayulins (5.0 g). The solid matrix was then washed with 200 mL of ethyl acetate, thus recovering argentatin B (2.3 g).

EXAMPLE 4

Liquid-liquid partitioning of the polar fraction (FIG. 1)

1.2 L of methanol/water 4:1 solution obtained from the first process of partitioning of the liquid-liquid type described in the example 2, were subjected to a further partitioning process with cyclohexane (200 mL).

After having reached the equilibrium between the phases, the organic phase was separated from the aqueous phase. The latter was extracted again with 200 mL of cyclohexane for 3 times.

The resultant organic phase was then washed with 200 mL of a mixture of methanol/water (4:1), recovered, anhydrified and concentrated at low pressures up to the complete drying thus obtaining 5.25 g of extract.

The methanol phase of the partitioning, comprising argentatins C and D, was extracted with 200 mL of ethyl acetate for 3 times, anhydrified and concentrated under low pressures up to the complete drying thus obtaining 1.77 g of extract.

The partitioning process was monitored by TLC (Thin layer chromatography).

EXAMPLE 5

Direct crystallization of guayulins and argentatins (FIG. 1)

a. Guayulin A: 5.0 g of guayulin mixture obtained by partitioning of the solid-liquid type described in the example 3, were dissolved in 10 mL of n-hexane. A copious precipitate was obtained by cooling the solution at −23° C. (acetone and dry ice-bath), which was then recovered by filtration.

The residue was washed with n-hexane at −23° C. up to the obtaining of a white crystalline product identified as guayulin A (3.2 g). IR ν max (KBr): 3081, 2977, 2925, 2860, 1709, 1640, 1496, 1310, 1180, 927, 766, 708, 662, 563, 486 cm$^{-1}$. $^1$H NMR (250 MHz, CDCl$_3$) δ ppm: 1.08 (s, 1H), 1.13 (s, 1H), 1.55 (d, J=1.2 Hz, 3H), 1.67 (d, J=1.4 Hz, 3H), 2.79 (dd, J=12.3, 5.3 Hz, 2H), 4.52 (d, J=11.6 Hz, 1H), 4.92 (td, J=11.1, 5.3 Hz, 2H), 5.12 (m), 6.43 (d, J=16 Hz, 1H), 7.40 (m, 3H), 7.50 (m, 2H). $^{13}$C NMR (75 MHz, CDCl$_3$) δ ppm: 166.2; 144.3; 135.8; 134.5; 130.1; 130.0; 128.8; 128.1; 128.0; 125.0; 118.7; 75.4; 42.9; 40.3; 32.9; 28.8; 28.5; 25.2; 21.4; 20.4; 16.5; 15.4.

The supernatant was recovered and the solvent was evaporated under reduced pressures thus obtaining 1.3 g of a mixture of guayulins A and B.

b. Argentatin B: 2.3 g of argentatin fraction obtained by the partitioning of the solid-liquid type described in the example 3, were dissolved in 10 mL of petroleum ether. A copious precipitate was obtained by cooling the solution at 0° C. (ice bath), which was then recovered by filtration.

The residue was washed with petroleum ether at 0° C. up to the obtaining of a white crystalline product identified as argentatin B (2.2 g). IR ν max (KBr): 3523, 3048, 2967, 2871, 2723, 1704, 1448, 1372, 1336, 1244, 1171, 1112, 1059, 910, 578 cm-1. $^1$H-NMR (250 MHz, CDCl$_3$); δ ppm: 4.55 (m, 1H,), 3.56 (dd, 5, 5, 1H), 1.11 (s, 3H), 1.07 (s, 3H), 1.06 (s, 3H), 0.92 (s, 3H), 0.87 (d, 7, 3H), 0.85 (s, 3H), 0.83 (s, 3H), 0.51 (d, 5, 1H) and 0.31 (d, 5, 1H). $^{13}$C-NMR (75 MHz, CDCl$_3$); δ ppm: 18.83, 19.51, 20.8, 21.03, 21.12, 21.65, 22.24, 23.68, 24.06, 25.15, 26.25, 26.32, 26.42, 29.27, 29.78, 32.93, 33.62, 35.79, 37.66, 45.07, 46.06, 47.73, 48.67, 50.35, 57.61, 75.14, 80.14, 92.93, 217.00.

c. Argentatin A: 5.25 g of extract derived from the organic phase obtained by the process of partitioning of the liquid-liquid type described in the example 4, were dissolved in 30 mL of ethyl ether. The solution was cooled at −23° C.

(acetone and dry ice-bath) and n-hexane was slowly added as long as a turbidity of the solution with the consequent precipitation of argentatin A was observed.

The precipitate was recovered by filtration and then it was subjected to washes with ethyl ether and n-hexane up to obtain a white crystalline product.

0.3 g of product identified as argentatin A were obtained. IR vmax (KBr): 3386, 2966, 2870, 1705, 1462, 1380, 1249, 1175, 1051, 954, 890, 837 cm$^{-1}$. $^1$H-NMR (250 MHz, CDCl$_3$); δ ppm: 3.83 (dd, 11, 1H), 3.58 (m, 1H), 1.67 (s, 3H), 1.43 (s, 3H), 1.27 (s, 3H), 1.23 (s, 3H), 1.12 (s, 3H), 1.11 (s, 3H), 0.92 (s, 3H), 0.77 (d, 7, 1H), 0.43 (d, 7, 1H). $^{13}$C-NMR (75 MHz, CDCl$_3$); δ ppm: 20.4, 20.9, 21.1, 21.5, 23.9, 25.6, 26.0, 26.2, 26.4, 26.7, 27.4, 30.2, 33.4, 37.4, 37.6, 46.6, 46.7, 47.8, 48.7, 50.3, 56.1, 70.9, 73.4, 87.2, 84.7, 216.1.

d. Argentatins C and D: 1.77 g of extract derived from the aqueous phase obtained from the process of partitioning of the liquid-liquid type described in the example 4, were dissolved in 10 mL of petroleum ether.

A white precipitate was obtained by cooling the solution at −23° C. (acetone and dry ice-bath), which was then recovered by filtration. The residue was washed with petroleum ether at −23° C. up to the obtaining of a white crystalline product identified as argentatin D (0.54 g). IR v max (KBr): 3499, 3036, 2972, 2922, 2862, 1710, 1440, 1337, 1162, 1111, 1055, 913, 779, 564 cm$^{-1}$. $^1$H-NMR (250 MHz, CDCl$_3$); δ ppm: 4.55 (m, 1H), 3.56 (dd, 5, 5, 1H), 3.44 (br t, 1H), 1.11 (s, 3H), 1.07 (s, 3H), 1.06 (s, 3H), 0.92 (s, 3H), 0.87 (d, 7, 3H), 0.85 (s, 3H), 0.83 (s, 3H), 0.51 (d, 5, 1H), 0.31 (d, 5, 1H). $^{13}$C-NMR (75 MHz; CDCl$_3$): δ ppm: 18.83, 19.51, 20.85, 21.03, 21.12, 21.65, 22.24, 23.68, 24.06, 25.15, 26.25, 26.32, 26.42, 29.27, 29.78, 32.93, 33.62, 35.79, 37.66, 45.07, 46.06, 47.73, 48.67, 50.35, 57.61, 75.14, 78.9, 80.14, 92.93.

The supernatant derived from the purification process of the argentatin D was recovered and the solvent was completely evaporated under reduced pressures. The residue was dissolved in 10 mL of ethyl ether.

The solution was cooled at −23° C. (acetone and dry ice-bath) and n-hexane was slowly added as long as a turbidity of the solution and the consequent precipitation of argentatin C were observed.

The precipitate was recovered by filtration and then it was subjected to washes with ethyl ether and n-hexane up to obtain a white crystalline product. The supernatant was recovered and re-crystalized in order to recover further product.

0.2 g of product identified as argentatin C were obtained. IR vmax (KBr): 3346, 2936, 2870, 1714, 1455, 1373, 1288, 1167, 1098, 1064, 917, 732, 669, cm$^{-1}$. $^1$H-NMR (250 MHz, CDCl$_3$); δ ppm: 4.55 (m, 1H), 3.58 (s, 2H), 3.56 (dd, 5, 5, 1H), 1.11 (s, 3H), 1.07 (s, 3H), 1.06 (s, 3H), 0.92 (s, 3H), 0.87 (d, 7, 3H), 0.85 (s, 3H), 0.83 (s, 3H), 0.51 (d, 5, 1H) 0.31 (d, 5, 1H).

EXAMPLE 6

Figure 4:
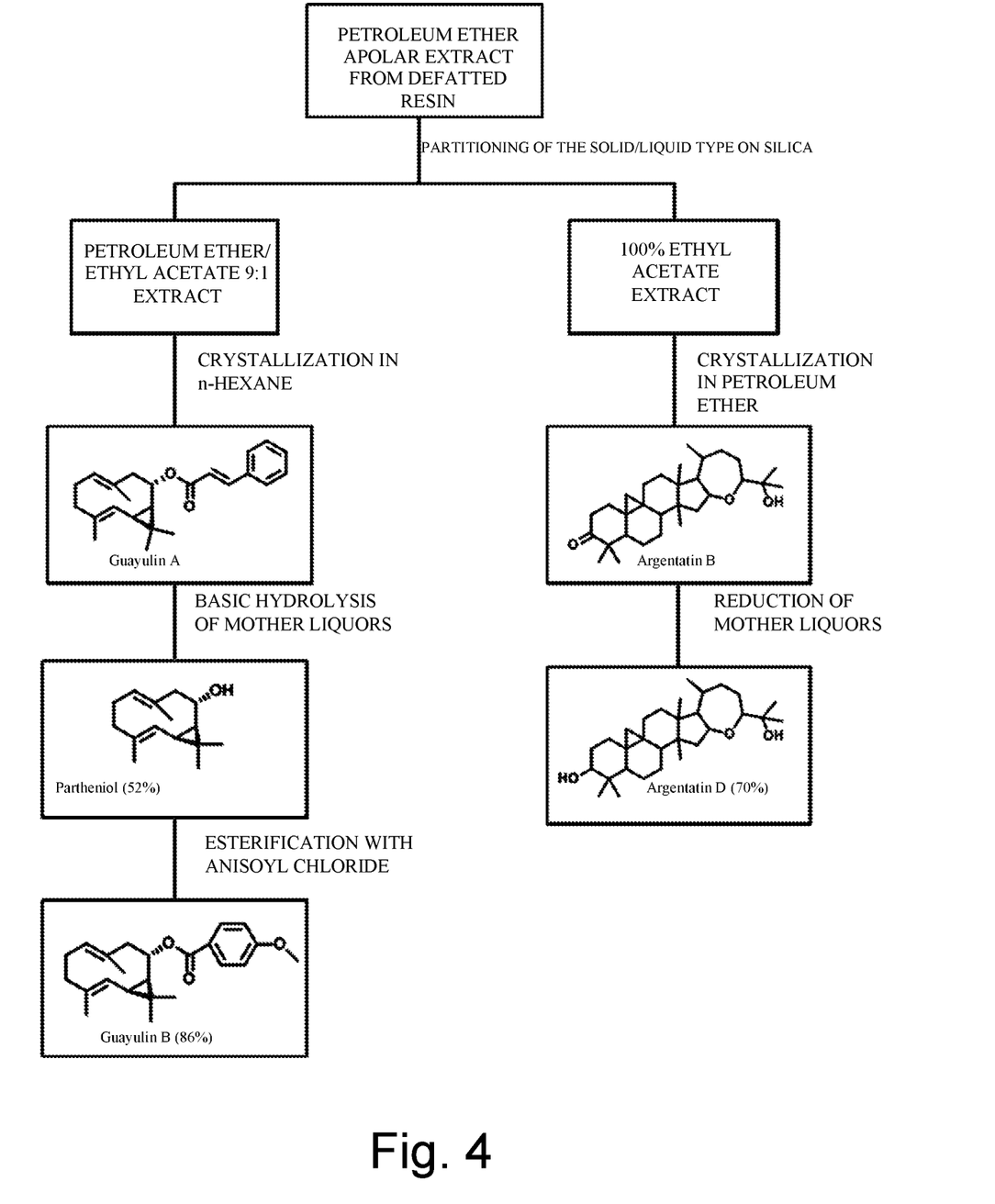
FIG. 4 represents a partial block-diagram of an embodiment of the method of the present invention, which shows the semi-synthesis of lower natural guayulins and argentatins starting from the non-polymer higher isoprenic constituents (guayulin A and argentatin B) separated and purified by the method of the present invention. The numbers in brackets represent the yield by weight of the depicted products obtained by semisynthesis.

Synthesis of the minor isoprenic constituents starting from the extracts (FIG. 4)

Starting from the guayulin mixture obtained as described in the example 3 or from the pure guayulin A obtained as described in the example 5 or from its mother liquors, it was possible to obtain natural products contained in the resin by semi-synthesis, wherein they are hardly obtainable by non-chromatographic methods, because of their lower concentrations.

a. Partheniol: Pure partheniol was obtained by basic hydrolysis reaction starting from the guayulin mixture obtained from the extract in petroleum ether/ethyl acetate 9:1 of the process of partitioning of the solid/liquid type or from pure guayulin A. 23.8 mL of a basic solution of potassium hydroxide and methanol (5% w/v; 425.4 mmol; 60 eqv) and 510 μL of water were added to 5.00 g of guayulin mixture. The reaction was maintained under stirring at 40° C. for 24 hours, monitoring its progress by TLC (Thin layer chromatography). The reaction was stopped by dilution with a saturated solution of water and sodium chloride and extracted with petroleum ether. The organic phase is anhydrified, filtered and the solvent was evaporated under reduced pressures. The residue (5.0 g) was then purified by crystallization in petroleum ether at 0° C. (into an ice-bath). A white crystalline product was obtained (2.6 g) identified as partheniol or deacylguayulin. IR v max (KBr): 3294, 3014, 2976, 2924, 2854, 2730, 1654, 1454, 1204, 1004, 851, 655, 534 cm$^{-1}$. $^1$H-NMR (250 MHz, CDCl$_3$); δ ppm: 0.73 (dd), 1.15 (s), 1.16 (s), 1.19 (s), 1.42 (dd), 1.44 (s), 1.63 (s), 3.6 (ddd), 4.36 (d), 4.91 (dd). $^{13}$C-NMR (75 MHz; CDCl$_3$): δ15.5, 16.5, 20.5, 20.8, 25.3, 28.8, 29.2, 36.0, 40.5, 46.3, 72.6, 125.3, 126.9, 129.2, 136.9.

b. Guayulin B: to a solution of 100 mg of anisic acid (molecular mass 152.15; 0.657 mmol) dissolved in 2 mL of dichloromethane, 380 μL of a solution of 98% oxalyl chloride in dichloromethane (molecular mass 126.93; density 1.335 g/mL; 2.63 mmol; 4 equivalents) and 66 μL of DMF (100 μL/mmol of acid) were added at 0° C. and under stirring for 1 hour. The reaction was maintained under stirring at room temperature for further 2.5 hours thus monitoring the development by TLC (Thin layer chromatography). The reaction was stopped by solvent evaporation under reduced pressures thus obtaining 100 mg of anisoyl chloride. Later, 77 mg of anisoyl chloride (molecular mass 170.15; 0.454 mmol; 1 equivalent) were added to a solution of 100 mg of partheniol (molecular mass 220.35; 0.454 mmol) dissolved in 6 mL of pyridine. The reaction was maintained under stirring at room temperature for 4 hours thus monitoring the development by TLC (Thin layer chromatography). The reaction was stopped by dilution with a saturated solution of water and sodium chloride and extracted with petroleum ether. The organic phase was anhydrified, filtered and the solvent was evaporated under reduced pressure. The residue was then purified by crystallization in petroleum ether at 0° C. (into an ice bath). A white crystalline product (0.15 g), identified as guayulin B, was obtained. IR vmax (KBr): 3504, 2932, 2854, 2790, 2657, 2123, 1707, 1606, 1449, 1359, 1166, 1045, 890, 770, 645, 539 cm$^{-1}$. $^1$H-NMR (250 MHz, CDCl$_3$); δ ppm: 1.08 (s), 1.13 (s), 1.55 (d, J=1.2 Hz, 3H), 1.67 (d, J=1.41 Hz, 3H), 2.79 (dd, J=12.3, 5.3 Hz, 2H), 3.85 (s), 4.52 (d, J=11.6 Hz, 1H), 4.92 (td, J=11.1, 5.3 Hz, 2H), 5.12 (m), 6.82 (d, J=9 Hz, 1H), 7.95 (d, J=9 Hz, 2H).

c. Semisynthetic argentatin D: To a solution of 100 mg of argentatin B (molecular mass 456.70; 0.218 mmol) obtained by the partitioning of the solid-liquid type described in the example 4 or from the mother liquors derived from the process of crystallization described in the example 5, dissolved in 4 mL of methanol, 25 mg of sodium borohydride NaBH$_4$ (molecular mass 37.83; 0.661 mmol; 3.0 equivalents) were slowly added, into an ice-bath at 0° C. The reaction was maintained under stirring at room temperature for 5 minutes, monitoring the development by TLC (Thin layer chromatography). The reaction was stopped by dilution with a saturated solution of water and sodium chloride, addition of a solution of water and 5% sulfuric acid up to neutral pH and extraction of the aqueous phase with ethyl acetate. The organic phase was anhydrified, filtered and the solvent was evaporated under reduced pressures. The residue was then purified by crystallization in petroleum ether at 0° C. (into an ice-bath). A white crystalline product (0.070 g) identified as argentatin D, was obtained. IR ν max (KBr): 3499, 3036, 2972, 2922, 2862, 1710, 1440, 1337, 1162, 1111, 1055, 913, 779, 564 cm$^{-1}$. $^1$H-NMR (250 MHz, CDCl$_3$); δ ppm: 4.55 (m, 1H), 3.56 (dd, 5, 5, 1H), 3.44 (br t, 1H), 1.11 (s, 3H), 1.07 (s, 3H), 1.06 (s, 3H), 0.92 (s, 3H), 0.87 (d, 7, 3H), 0.85 (s, 3H), 0.83 (s, 3H), 0.51 (d, 5, 1H), 0.31 (d, 5, 1H). $^{13}$C-NMR (75 MHz; CDCl$_3$): δ ppm: 18.83, 19.51, 20.85, 21.03, 21.12, 21.65, 22.24, 23.68, 24.06, 25.15, 26.25, 26.32, 26.42, 29.27, 29.78, 32.93, 33.62, 35.79, 37.66, 45.07, 46.06, 47.73, 48.67, 50.35, 57.61, 75.14, 78.9, 80.14, 92.93.

EXAMPLE 7

Figure 2:
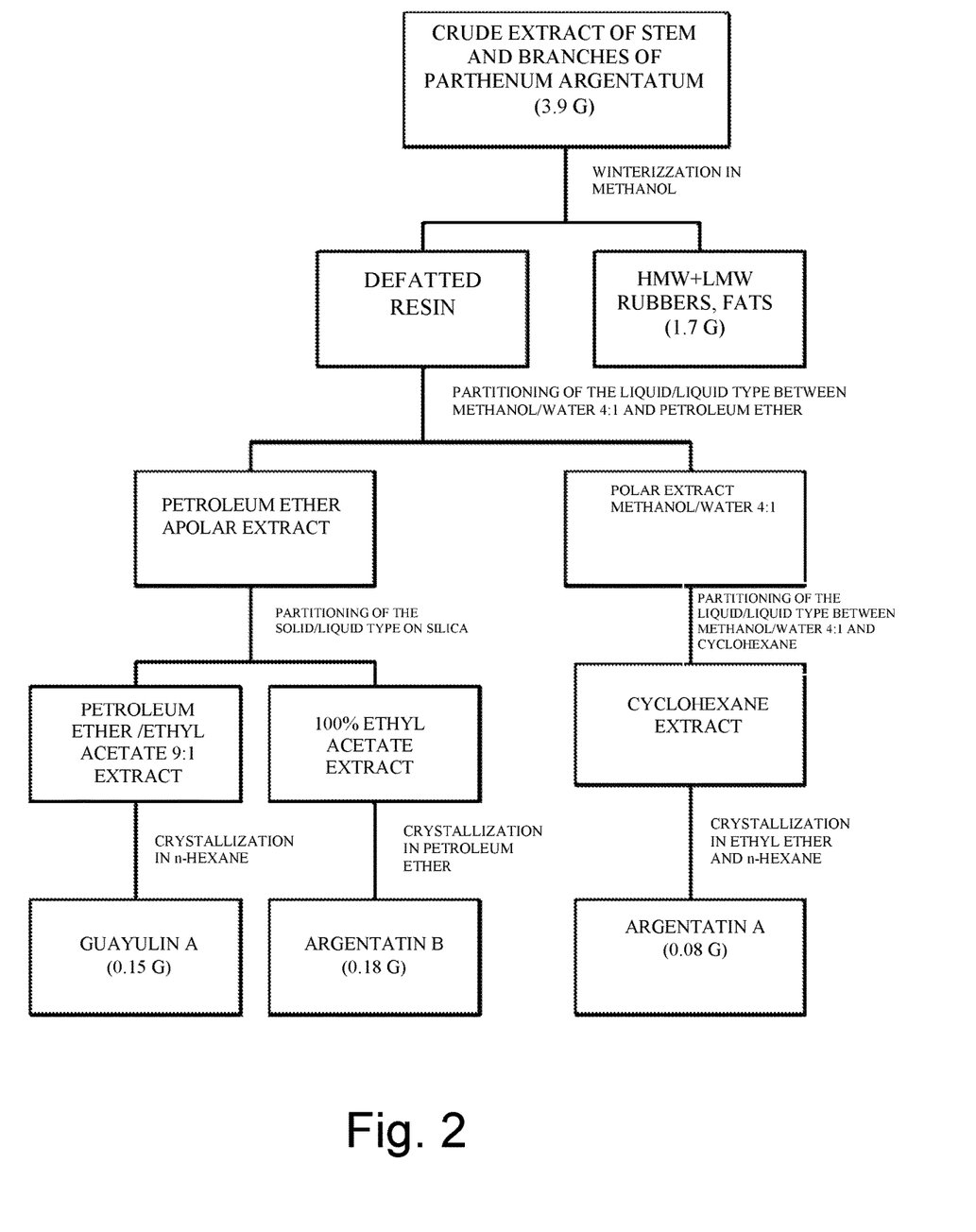
FIG. 2 represents a block-diagram of an embodiment of the method of the present invention, starting from a crude extract obtained from branches and stem of *Parthenium argentatum*, which shows the obtaining of guayulin A, and argentatin A and B. The numbers in brackets represent the amount of product expressed in grams.

Plant material: crude extract of branches and stems of *parthenium argentatum* (FIG. 2)

3.89 g of crude extract, obtained from branches and stem of *Parthenium argentatum* were processed in accordance with this invention for separating guayulin A and argentatins A and B. Following the separation process of the lipophilic component comprising fats and low molecular weight rubbers, by the winterization method, the processes of separation and direct crystallization with the same procedures described in the Examples 2-6 and in relation to the amount of the crude extract used, were carried out. 1.7 g of lipophilic mixture of fats and low molecular weight and high molecular weight (HMW) rubbers, 0.15 g of crystalline guayulin A, 0.08 g of argentatin A, 0.18 g of argentatin B, were obtained.

EXAMPLE 8

Figure 3:
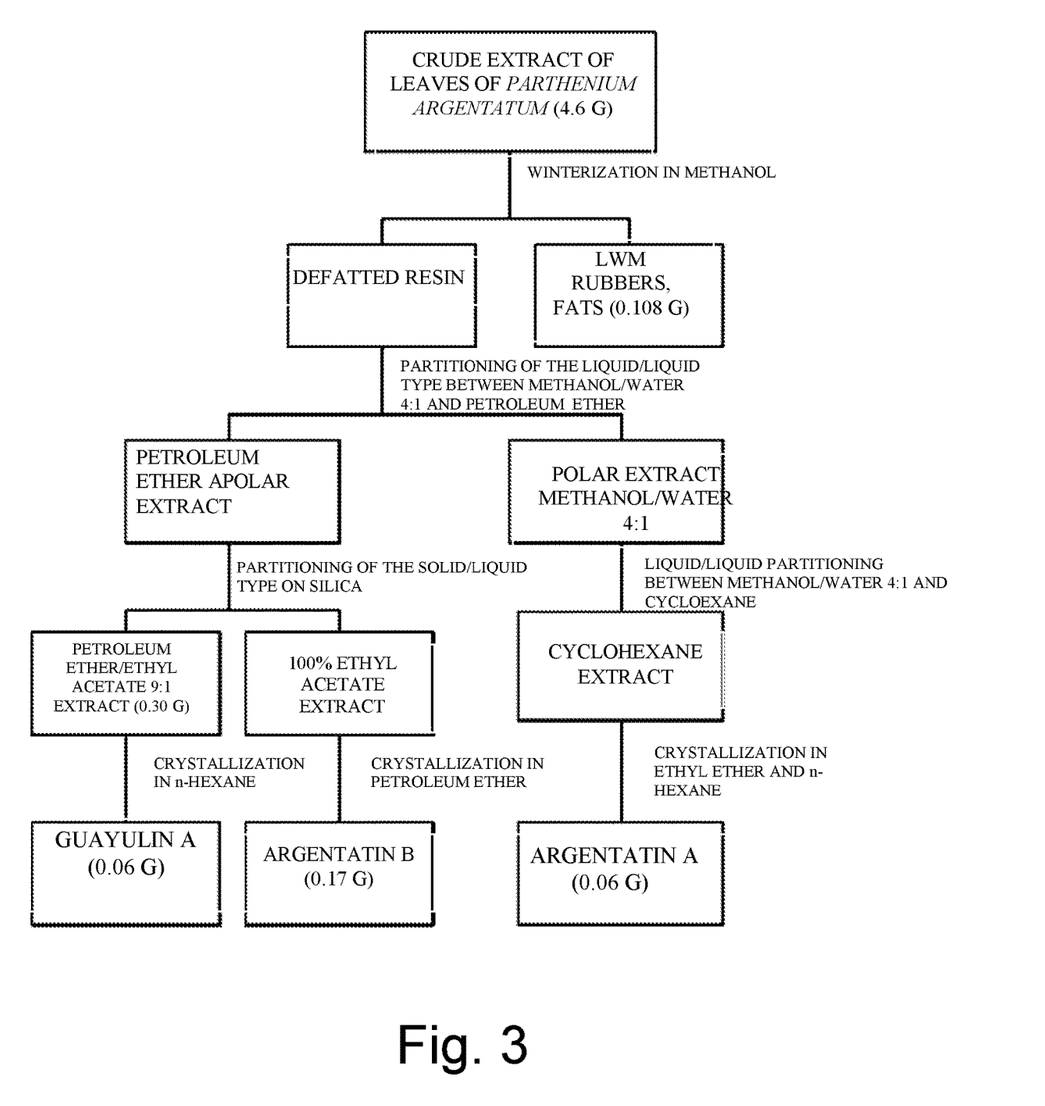
FIG. 3 represents a block-diagram of an embodiment of the method of the present invention, starting from a crude extract obtained from leaves of *Parthenium argentatum*, which shows the obtainment of guayulin A, and argentatin A and B. The numbers in brackets represent the amount of product expressed in grams.

Plant material: crude extract of *Parthenium argentatum* leaves (FIG. 3)

4.6 g of crude extract, obtained from leaves of Italian *Parthenium argentatum* from Basilicata, were processed in accordance with this invention, for separating the guayulins component and argentatins A and B. Following the separation process of the lipophilic component comprising fats and low molecular weight rubbers, by the winterization method, the processes of partitioning and direct crystallization with the same procedures described in the Examples 2-6 and in relation to the amount of the crude extract used, were carried out. 0.30 g of guayulin mixture were obtained, from which by direct crystallization with n-hexane at −23° C. (acetone and dry ice-bath) 0.06 g of crystalline guayulin A, 0.06 g of argentatin A and 0.17 g of argentatin B, were obtained.

EXAMPLE 9 (COMPARATIVE)

Liquid-liquid partitioning of a Non-winterized crude extract of *Parthenium argentatum*

5.0 g of crude extract obtained from the bagasse of *Parthenium argentatum* were slowly dissolved under continuous stirring at 40° C. in methanol (400 mL) using a solvent volume of 1.0 L/100 g of crude extract. After complete dissolution, the mixture was cooled at room temperature and diluted to a final volume of 500 mL with 100 mL of water, obtaining a mixture methanol/water (4:1).

The obtained mixture was subjected to a partitioning process with petroleum ether (100 mL). 250 mL of methanol/water (4:1) mixture were further added to the mixture, and finally the establishment of an equilibrium between the phases was obtained; thereafter the organic phase was separated from the aqueous phase.

The latter was subjected again to extraction with 100 mL of petroleum ether for six times. The resulting organic phase was subsequently washed with 200 mL of a methanol/water (4:1) mixture, recovered, anhydrified and concentrated under reduced pressure till complete drying, obtaining 2.5 g of product. The partitioning process was monitored through TLC (Thin layer chromatography).

EXAMPLE 10 (COMPARATIVE)

Solid-Liquid Partitioning of the Apolar Extract Deriving from a Non-Winterized Crude Extract of *Parthenium Argentatum*

2.5 g of apolar extract obtained from the liquid-liquid partitioning process of 5.0 g of crude extract obtained as described in comparative Example 9 were dissolved in 20 mL of a mixture of petroleum ether and ethyl acetate (9:1) and adsorbed on a bed of 70 mL of silica gel (70-230 mesh, 25 mL/g). The solvent was removed from the suspension by evaporation under reduced pressure or by filtration under vacuum, and the resulting solid matrix was washed three times with 100 mL of the solvent mixture used for adsorption.

The process resulted difficult and ineffective, as any efficient separation of the components of the starting apolar crude extract could not be observed, due to the presence of a component consisting of fats and low molecular weight rubbers, which negatively affected the solid-liquid partitioning process.

EXAMPLE 11 (COMPARATIVE)

Liquid-liquid partitioning of the polar fraction deriving from a non-winterized crude extract of *Parthenium argentatum*

950 mL of a methanol/water (4:1) solution obtained from the first liquid-liquid partitioning process described in comparative Example 9 were subjected to a further partitioning process with 100 mL of cyclohexane. After the establishment of an equilibrium between the phases, the organic phase was separated from the aqueous phase. The latter was subjected again to extraction with 100 mL of cyclohexane, for three times. The resulting organic phase was subsequently washed with 100 mL of a methanol/water (4:1) mixture, recovered, anhydrified and concentrated under low pressure till complete drying, obtaining 300 mg of extract. The methanol phase from the partitioning, comprising argentatins C and D, was extracted with 100 mL of ethyl acetate for three times, anhydrified and concentrated under low pressure till complete drying, obtaining 100 mg of extract.

EXAMPLE 12 (COMPARATIVE)

Crystallization of guayulins and argentatins from extracts deriving from a non-winterized crude extract of *Parthenium argentatum* a. Guayulin A and argentatin B: 2.5 g of apolar extract obtained from the liquid-liquid partitioning described in comparative Example 9, were dissolved in 10 mL of n-hexane. By chilling the solution to −23° C. (into a dry ice/acetone bath) the expected formation of any precipitate of guayulin A and/or argentatin B could not be observed.

b. Argentatin A: 300 mg of extract deriving from the organic phase obtained from the liquid-liquid partitioning process described in comparative Example 11, were dissolved in 5 mL of ethyl ether. The solution was chilled to −23° C. (into a dry ice/acetone bath) and n-hexane was slowly added until a faint turbidity of the solution, resulting in an inefficient precipitation of argentatin A, was observed.

c. Argentatins C and D: 100 mg of extract deriving from the aqueous phase obtained from the liquid-liquid partition process described in comparative Example 11, were dissolved in 2 mL of petroleum ether. After chilling the solution to −23° C. (into a dry ice/acetone bath) no precipitate formation was observed.

These comparative examples clearly demonstrate that omitting the crucial winterization step from the separation method of the present invention results in a drastic reduction of its effectiveness in obtaining the isoprenic constituents of guayule or guayule-like resin in purified form.

The invention claimed is:

1. A method for separating at least one isoprenic constituent from a resin of a guayule (*Parthenium argentatum*) and/or of a guayule type plant selected from the group consisting of *Euphorbia lathyris, Parthenturr incanum, Chrysothamnus nauseosus, Pedilanthus macrocarpus, Cryptostegia grandiflora, Asclepias syriaca, Asclepius speciosa, Asclepias subulata, Solidago altissima, Solidago gramnifblia, Salidago rigida, Cacalia atriplicifolia, Taraxacum koksaghyz, Pvcnanthemum incanum, Teucreum canadence* and *Campanula Americana*, the method comprising:
 a) forming a defatted resin of the guayule and/or the guayule type plant;
 b) liquid-liquid partitioning the defatted resin with solvents that are immiscible in each other to obtain: an apolar extract comprising the isoprenic constituents guayulin A, guayulin B and argentatin B; and a polar extract comprising the isoprenic constituents argentatin A, argentatin C and argentatin D; and
 c) separating at least one isoprenic constituent from the polar extract, the apolar extract, or both,
 wherein the separating c) comprises: liquid-liquid partitioning the polar extract with solvents that are immiscible in each other, solid-liquid partitioning the apolar extract, or a combination thereof.

2. The method according to claim 1, wherein the at least one isoprenic constituent is selected from the group consisting of guayulin A, guayulin B, argentatin A, argentatin B, argentatin C, argentatin D, and mixtures thereof.

3. The method according to claim 1, wherein the defatted resin is obtained by defatting a crude extract of the guayule, the guayule type plant, or both.

4. The method according to claim 1, wherein, in the liquid-liquid partitioning b), the solvents that are immiscible in each other comprise a polar solvent and an apolar solvent.

5. The method according to claim 1, wherein:
 the separating c) comprising the solid-liquid partitioning of the apolar extract; and
 the solid-liquid partitioning comprises:
  subjecting the apolar extract, dissolved in a combination of two solvents miscible in each other, to adsorption on a solid matrix, and
  treating the solid matrix thus obtained with a combination of two solvents miscible in each other, to obtain a solution comprising a mixture of guayulin A and guayulin B, and a solid matrix comprising argentatin B.

6. The method according to claim 5, wherein the solid matrix comprising argentatin B is further treated to obtain a solution of argentatin B.

7. The method of claim 1, wherein:
 the separating c) comprises the liquid-liquid partitioning of the polar extract; and
 the liquid-liquid partitioning comprises separating the polar extract in a combination of a polar solvent and an apolar solvent to obtain an organic phase comprising argentatin A and an aqueous phase comprising a mixture of argentatin C and argentatin D.

8. The method according to claim 7, wherein in the liquid-liquid partitioning c):
 the apolar solvent is selected from the group consisting of cyclohexane, n-hexane, petroleum ether, and combinations thereof; and
 the polar solvent is selected from the group consisting of water, methanol, ethanol, isopropanol, tert-butanol, and combinations thereof.

9. The method according to claim 1, further comprising:
 d) purifying at least one isoprenic constituent obtained in the separating c).

10. The method according to claim 9, wherein the purifying d) comprises crystallizing at least one isoprenic constituent, to obtain the at least one isoprenic constituent in substantially pure crystalline form.

11. The method according to claim 9, wherein the purifying d) comprises d1) subjecting a mixture of guayulin A and guayulin B obtained in the separating c) to precipitation of the guayulin A by treatment with an apolar solvent with cooling, to obtain a precipitate of purified guayulin A and a supernatant comprising a mixture of guayulin A and guayulin B.

12. The method according to claim 9, Wherein the purifying d) comprises d2) precipitating the argentatin B obtained in the separating c) with an apolar solvent with cooling, to obtain a precipitate of purified argentatin B.

13. The method according to claim 9, wherein the purifying d) comprises d3) precipitating the argentatin A obtained in the separating c) an apolar solvent with cooling, to obtain a precipitate of purified argentatin A.

14. The method according to claim 9, wherein the purifying d) comprises d4) precipitating a mixture of argentatin C and argentatin D obtained in the separating c) with an apolar solvent with cooling, to obtain a precipitate of purified argentatin D and a supernatant comprising argentatin C.

15. The method according to claim 14, wherein the precipitating d4) is followed by evaporating d5) solvent of the supernatant and dissolving the residue in an apolar solvent with cooling, to obtain a precipitate of purified argentatin C C.

16. The method of claim 11, wherein the separating c) is followed by e1) performing a base hydrolysis reaction of the guayulin A obtained in the precipitation d1) and/or of the mixture of guayulin A and guayulin B obtained in the separating c) to obtain a solution comprising partheniol.

17. The method according to claim 16, wherein the base hydrolysis reaction e1) is followed by e2) esterification of the thus obtained partheniol.

18. The method according to claim 17, further comprising evaporating a solution comprising guayulin B obtained in the esterification e2), and dissolving a resulting residue in an apolar solvent to obtain a precipitate of purified guayulin B.

19. The method according to claim 12, wherein the separating c) is followed by e3) performing a reduction reaction of the argentatin B obtained in the separating c) and/or in the precipitating d2), to obtain a solution comprising argentatin D.

20. The method according to claim 19, wherein, following the reduction reaction, the solution comprising argentatin D is evaporated and a resulting residue is dissolved in an apolar solvent, to obtain a precipitate of purified argentatin D.

* * * * *